(12) United States Patent
Herwig

(10) Patent No.: US 8,317,101 B2
(45) Date of Patent: Nov. 27, 2012

(54) PRODUCE DATA COLLECTER WHICH COLLECTS INTERNAL PRODUCE INFORMATION

(75) Inventor: Nathaniel Christopher Herwig, Lawrenceville, GA (US)

(73) Assignee: NCR Corporation, Duluth, GA (US)

( * ) Notice: Subject to any disclaimer, the term of this patent is extended or adjusted under 35 U.S.C. 154(b) by 126 days.

(21) Appl. No.: 12/617,221

(22) Filed: Nov. 12, 2009

(65) Prior Publication Data
US 2010/0206951 A1 Aug. 19, 2010

Related U.S. Application Data

(60) Provisional application No. 61/152,759, filed on Feb. 16, 2009.

(51) Int. Cl.
*G06K 7/00* (2006.01)
(52) U.S. Cl. .................................. 235/439; 454/462.25
(58) Field of Classification Search ................. 235/439, 235/454, 455, 462.25, 462.41, 462
See application file for complete search history.

(56) References Cited

U.S. PATENT DOCUMENTS

| 5,979,240 | A | * | 11/1999 | Rix et al. ......................... 73/602 |
| 6,505,775 | B1 | * | 1/2003 | Gu et al. ......................... 235/454 |
| 2005/0206500 | A1 | * | 9/2005 | Ferren et al. ................. 340/5.82 |
| 2007/0285256 | A1 | * | 12/2007 | Batra .......................... 340/572.8 |
| 2009/0140046 | A1 | * | 6/2009 | Landers et al. ............... 235/385 |

* cited by examiner

*Primary Examiner* — Daniel St. Cyr
(74) *Attorney, Agent, or Firm* — Paul W. Martin; Peter H. Priest

(57) ABSTRACT

A produce data collector which collects internal produce information. The produce data collector includes a sonograph for directing acoustic energy in the form of sound waves into a produce item, for receiving return sound waves from the produce item, for converting the return sound waves into electrical signals, and for sending the electrical signals to a computer that identifies the produce item.

13 Claims, 2 Drawing Sheets

PRODUCE DATA COLLECTER WHICH COLLECTS INTERNAL PRODUCE INFORMATION

CROSS-REFERENCE TO RELATED APPLICATIONS

The present application claims the benefit of the filing date of Provisional Application Ser. No. 61/152,759, filed Feb. 16, 2009, under the same title.

BACKGROUND

One of the most frustrating problems facing grocery retailers is the lack of an automatic, accurate and efficient method to identify fruits and vegetables at the checkout (or self-checkout) lane. Many manual methods exist, but all are slow and inaccurate. The most common method involves consulting a printed list of all fruits and vegetables sold in a given store, to find their corresponding price codes. Since the process is so inefficient, many cashiers simply guess at the price codes or simply memorize and use a small subset of common price codes—especially if there are long lines at the register. This means the retailer loses revenue if the item actually sold is a more expensive item. For this reason, speed and accuracy are both important.

There have been attempts at solving this problem. U.S. Pat. No. 6,332,573 discloses one such device which analyzed spectral characteristics of light reflected from produce items.

It would be desirable to provide a produce data collector that alone or in combination with other types of produce data collectors addresses these concerns.

SUMMARY

A produce data collector which collects internal produce information is provided.

The produce data collector may include a sonograph for directing acoustic energy in the form of sound waves into a produce item, for receiving return sound waves from the produce item, for converting the return sound waves into electrical signals, and for sending the electrical signals to a computer that identifies the produce item.

DETAILED DESCRIPTION

Figure 1:
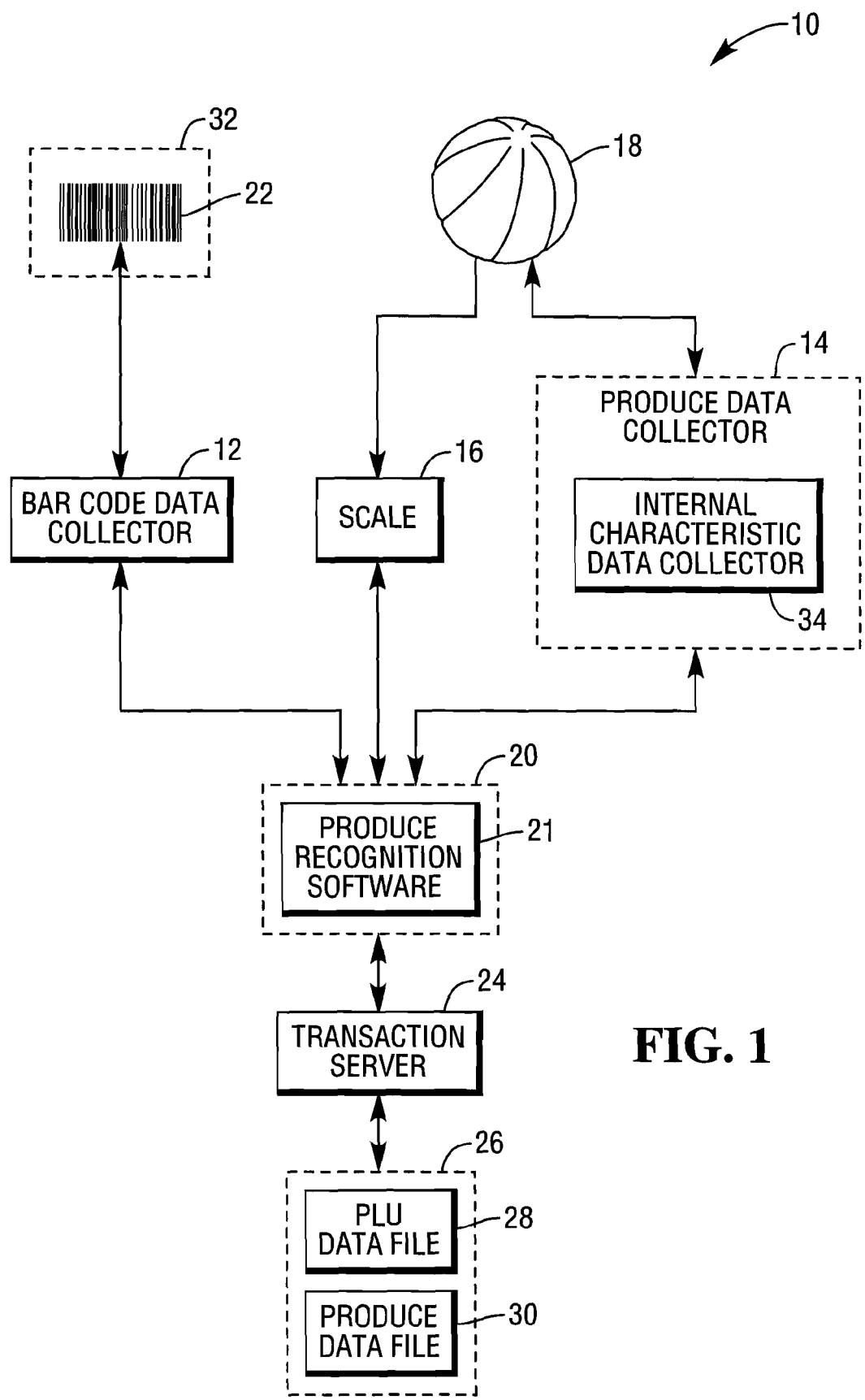
FIG. 1 illustrates an example transaction system.

Referring now to FIG. 1, transaction processing system 10 includes produce data collector 14 and scale 16.

Produce data collector 14 collects data for produce item 18. Produce data collector 14 includes internal characteristic collector 34, which captures data about the internal characteristics of produce item 18. An example internal characteristic collector 34 may receive and process sound waves directed at produce item 18. Another example internal characteristic collector 34 may receive and process electromagnetic waves directed at produce item 18.

Produce data collector 14 may capture additional information about produce item 18, such as any one or a combination of color and color distribution data, size data, shape data, surface texture data, and aromatic data.

Produce data collector 14 may be integrated into bar code data collector 12 or operated outside of barcode data collector 12.

Scale 16 determines a weight for produce item 18. Scale 16 may work in connection with a bar code data collector 12, but may be designed to operate and be mounted separately. Scale 16 sends weight information for produce item 18 to transaction terminal 20 so that transaction terminal 20 can determine a price for produce item 18 based upon the weight information. Produce recognition software 21 may additionally use weight information to help identify produce item 18.

During a transaction, operation of produce data collector 14 may be initiated by placement of produce item 18 on scale 16 or by operator-initiated commands from transaction terminal 20.

Transaction terminal 20 may include a self-service checkout terminal or an assisted-service checkout terminal.

In an example embodiment, transaction terminal 20 executes produce recognition software 21 which obtains produce characteristics from produce data collector 14, identifies produce item 18 by comparing produce data in produce data file 30 with collected produce data, retrieves an item identification number from produce data file 30 and a corresponding price from PLU data file 28.

In an alternative embodiment, identification of produce item 18 may be handled by transaction server 24. Transaction server 24 may receive collected produce characteristics and compares them with produce data in produce data file 30. Following identification, transaction server 24 may obtain a price for produce item 18 and forward it to transaction terminal 20.

To assist in proper identification of produce items, produce recognition software 21 may additionally display candidate produce items for operator verification. Produce recognition software 21 preferably arranges the candidate produce items in terms of probability of match and displays them as text and/or color images on an operator display of transaction terminal 20. The operator may accept the most likely candidate returned by or override it with a different choice.

Transaction processing system 10 may additionally include bar code data collector 12. Bar code data collector 12 reads bar code 22 on merchandise item 32 to obtain an item identification number, also known as a price look-up (PLU) number, associated with item 32. Barcode reader 22 may include any type of technology for reading barcode 22 on item 32, including but not limited to laser-based barcode reading technologies, image-based barcode reading technologies, and combinations of both laser and image-based barcode reading technologies. Bar code data collector 12 may be located within a checkout counter or mounted on top of a checkout counter.

Bar code data collector 12 and produce data collector 14 may be integrated into a common housing. Bar code data collector 12 and produce data collector 14 may share a common control circuitry or operate separately from each other. Alternatively, produce data collector 14 may be housed separately. For example, produce data collector 14 may include a hand-held produce data collector 14.

Transaction terminal 20 obtains the item identification number from bar code data collector 12 and retrieves a corresponding price from PLU data file 28 through transaction server 24.

PLU data file 28 and produce data file 30 are stored within storage medium 26, but either may be located instead at transaction terminal 20, or bar code data collector 12.

Figure 2:
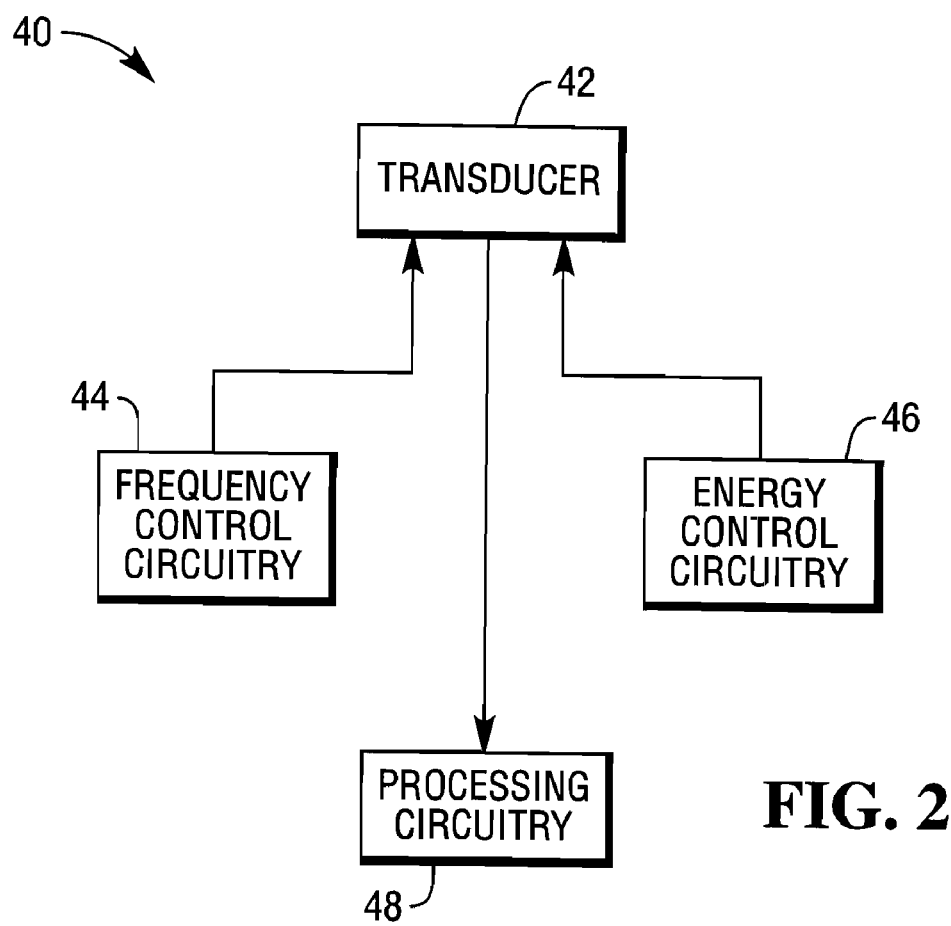
FIG. 2 is an example embodiment of a produce data collector.

Turning now to FIG. 2, an example internal characteristic collector 34 includes a sonograph 40.

Sonograph 40 includes a transducer 42. Transducer 42 converts electrical energy into acoustic energy in the form of sound waves, receives return sound waves from inside of produce item 18, and converts the acoustic energy in the return sound waves into electrical energy.

The frequency of the sound waves may be fixed to a frequency that provides sufficient resolution of internal characteristics of all produce items that are to be recognized.

Alternatively, sonograph 40 may additionally include frequency control circuitry 44, which adjusts the frequency of the sound waves.

Terminal 20 may control the frequency based upon operator responses to questions from terminal 20 as to the approximate size of produce item 18. Alternatively, an operator may control the frequency either via terminal selections or a control knob on sonograph 40.

Sonograph 40 may further include energy control circuitry 46 for controlling the acoustic energy produced by transducer 42.

The energy of the sound waves may be fixed to an energy level that provides a sufficient level of energy in returning sound waves captured from produce item 18. Alternatively, an operator may control the energy level either via terminal selections or a control knob on sonograph 40.

Sound waves are reflected anywhere there are density changes in produce item 18.

Sonograph 40 may include processing circuitry 48 for processing electrical signals from transducer 42 associated with returning sound waves to produce images.

Alternatively, a computer such as terminal 20 or server 24 may process the electrical signals to produce the images for display by terminal 20.

Produce recognition software 21 processes image information from internal characteristic collector 34 and other types of produce data collectors 14, if present, which may provide other types of information such as any one or a combination of color and color distribution data, size data, shape data, surface texture data, and aromatic data. Produce recognition software 21 may additionally use weight information to help identify produce item 18.

Although particular reference has been made to certain embodiments, variations and modifications are also envisioned within the spirit and scope of the following claims.

What is claimed is:

1. A transaction processing system comprising:
a produce data collector employing a sonograph for directing acoustic energy in the form of sound waves into a produce item, for receiving return sound waves from the produce item, for converting the return sound waves into electrical signals;
a computer that receives the electrical signals from the produce data collector and executes produce recognition software to identify the produce item; and
a produce data file storing an item identification number for the produce item.

2. The transaction processing system of claim 1 further comprising:
a price look-up file stored in a storage medium, the price look-up file including price data corresponding to the identification number for the produce item.

3. The transaction processing system of claim 2, wherein the computer utilizes the identification number for the produce item to retrieve a corresponding price from the price look-up tile.

4. The transaction processing system of claim 1 further comprising:
a bar code data collector.

5. The transaction processing system of claim 4 wherein the produce data collector and the bar code data collector are integrated in a common housing.

6. The transaction processing system of claim 5 wherein the bar code data collector is located within a checkout counter.

7. The transaction processing system of claim 1 further comprising:
a scale for producing a weight for the produce item, and wherein the produce recognition software further employs the weight to help identify the produce item.

8. The transaction processing system of claim 1 further comprising:
a scale for producing a weight for the produce item, and wherein operation of the produce data collector is initiated upon placement of the produce item on the scale.

9. The transaction processing system of claim 1, wherein said system is part of a self-service checkout terminal or an assisted-service checkout terminal.

10. The transaction processing system of claim 1, wherein the computer controls a display to display candidate produce items for operator verification.

11. The transaction processing system of claim 1, wherein the computer controls frequency of the sonograph based upon operator response to a question as to approximate size of the produce item.

12. The transaction processing system of claim 1, wherein the system displays candidate produce items for operator verification.

13. The transaction apparatus of claim 12 wherein the candidate produce items are arranged in terms of probability of match.

* * * * *